US007723078B2

(12) United States Patent
Dieman et al.

(10) Patent No.: US 7,723,078 B2
(45) Date of Patent: May 25, 2010

(54) METHOD FOR THE AMPLIFICATION AND DETECTION OF HBV DNA USING A TRANSCRIPTION BASED AMPLIFICATION

(75) Inventors: Birgit Alberta Louisa Maria Dieman, Oisterwijk (NL); Inge Marjolein Frantzen, Helmond (NL); Arnoldina Margaretha Wilhelmina Van Strijp, Den Bosch (NL)

(73) Assignee: Biomerieux, B.V., Boxtel (NL)

( * ) Notice: Subject to any disclaimer, the term of this patent is extended or adjusted under 35 U.S.C. 154(b) by 22 days.

(21) Appl. No.: 11/956,869

(22) Filed: Dec. 14, 2007

(65) Prior Publication Data

US 2008/0241891 A1 Oct. 2, 2008

Related U.S. Application Data

(62) Division of application No. 10/471,073, filed as application No. PCT/EP02/02600 on Mar. 6, 2002, now abandoned.

(30) Foreign Application Priority Data

Mar. 7, 2001 (EP) .................................. 01200855

(51) Int. Cl.
*C12Q 1/64* (2006.01)
*C12P 19/34* (2006.01)
(52) U.S. Cl. .......................... 435/91.2; 435/6; 435/91.1
(58) Field of Classification Search ...................... None
See application file for complete search history.

(56) References Cited

U.S. PATENT DOCUMENTS 5,679,510 A 10/1997 Ray et al.

(Continued)

FOREIGN PATENT DOCUMENTS

DE 19835856 * 2/2000

(Continued)

OTHER PUBLICATIONS

Rivkina et al (1988) Gene vol. 64: pp. 285-296.*
Custom digest of M21030 Apr. 2009.*
Aki et al. "Method for Assaying HBV Gene by Real Time Detection PCR Method and Primer and Probe to be Used Therein" Database EMBL Online' Acc. No. E25735 (Feb. 2001) (Abstract).

(Continued)

*Primary Examiner*—Young J Kim
(74) *Attorney, Agent, or Firm*—Myers Bigel Sibley & Sajovec, P.A.

(57) ABSTRACT

The present invention provides a method for the transcription based amplification of a target HBV nucleic acid sequence starting from HBV DNA optionally present in a sample, comprising the steps of, —incubating the sample, suspected to contain HBV, in an amplification buffer with one or more restriction enzymes capable of cleaving the HBV DNA at a selected restriction site, said restriction enzyme creating a defined 3' end of said HBV DNA stand(s), a promoter-primer, said promoter-primer having a 5' region comprising the sequence of a promoter recognized by a DNA-dependent RNA polymerase and a 3' region complementary to the define 3' end of the DNA strand, a second or reverse primer, having the opposite polarity of the promoter-primer and comprising the 5' end of the said target sequence, and in case of HBV ssDNA as the target sequence, a restriction primer, maintaining the thus created reaction mixture under the appropriate conditions for a sufficient amount of time for a digestion by the restriction enzyme to take place, subjecting the sample thus obtained to a heat treatment at a temperature and time sufficient to inactivate the restriction enzyme and/or to render at least partially a double strand single stranded, adding the following reagents to the sample: an enzyme having RNA dependent DNA polymerase activity, and maintaining the thus created reaction mixture under the appropriate conditions to a sufficient amount of time for the amplification to take place.

19 Claims, 6 Drawing Sheets

U.S. PATENT DOCUMENTS

| | | | |
|---|---|---|---|
| 5,736,316 A | | 4/1998 | Irvine et al. |
| 5,736,334 A | | 4/1998 | Spies |
| 5,972,607 A | * | 10/1999 | Kondo et al. ............... 435/6 |
| 5,981,179 A | | 11/1999 | Lorinez et al. |
| 7,122,364 B1 | | 10/2006 | Lyamichev et al. |

FOREIGN PATENT DOCUMENTS

| | | | |
|---|---|---|---|
| DE | 19835856 A1 | * | 2/2000 |
| EP | 0 397 269 | | 11/1990 |
| EP | 0 397 269 A1 | * | 11/1990 |
| WO | WO 91/04340 | | 4/1991 |
| WO | WO 9104340 | | 4/1991 |
| WO | WO 95/02690 | * | 1/1995 |
| WO | WO 99/25868 | | 5/1999 |
| WO | WO 02/070735 | | 9/2002 |

OTHER PUBLICATIONS

Fujiyama et al. "Cloning and Structural Analyses of Hepititis B Virus DNAs, Subtype *adr*" *Nucleic Acids Research* 11(13):4601-4610 (1983).

Kievits et al. "NASBA Isothermal Enzymatic In Vitro Nucleic Acid Amplification Optimized for the Diagnosis of HIV-1 Infection" *Journal of Virological Methods* 35:273-286 (1991).

International Search Report for International Application Serial No. PCT/EP02/02600, mailed Jun. 18, 2003.

Buck et al. "Design strategies and performance of custom DNA sequencing primers" *Biotechniques* 27(3):528-536 (1999).

SCORE Search result us-10-471-073-4.rge.

SCORE Search results us-10-471-073-5.rge.

* cited by examiner

METHOD FOR THE AMPLIFICATION AND DETECTION OF HBV DNA USING A TRANSCRIPTION BASED AMPLIFICATION

STATEMENT OF PRIORITY

The present application is a divisional application of, and claims priority to, U.S. application Ser. No. 10/471,073, filed Jul. 28, 2004 now abandoned, which is a 35 U.S. §371 National Phase Application of International Application Serial No. PCT/EP02/02600, file Mar. 6, 2002 and published in English as PCT Publication No. WO 02/072881 on Sep. 19, 2002, which claims priority to European Application Serial No. 01200855.3, filed Mar. 7, 2001, the disclosures of which are incorporated herein by reference in their entireties.

The present invention is directed to a transcription based amplification method for the amplification of HBV DNA.

Nucleic acid amplification methods are used in the field of molecular biology and recombinant DNA technology. These methods are used to increase the number of copies of a particular nucleic acid sequence, present in small amounts and often in an environment in which a wide variety of other nucleic acid sequences, both RNA and DNA, are also present. In particular, nucleic acid amplification methods are used to facilitate the detection or quantification of nucleic acid and are important for diagnosing for example infectious diseases, inherited diseases and various types of cancer. Nucleic acid amplification methods have also found their applications in other fields where samples are investigated in which nucleic acid may be present in minute amounts, such as forensic sciences, archeology or to establish paternity. Several nucleic acid amplification techniques are known based on different mechanisms of action. One method for the amplification of nucleic acid is known as the "Polymerase Chain Reaction" (PCR) is described in European patent applications EP 200362 and EP 201148.

The present invention is concerned with a different class of nucleic acid amplification methods namely the "transcription based amplification techniques". With these methods multiple RNA copies are obtained from a DNA template that comprises a functional promoter recognized by the RNA polymerase. Said RNA copies are used as target from which new DNA templates are obtained etc. Gingeras et al. in WO88/10315 and Burg et al. in WO89/1050 have described such methods. Isothermal transcription based amplification techniques have been described by Davey et al. in EP 323822 (relating to the NASBA method), by Gingeras et al. in EP 373960 and by Kacian et al. in EP 408295. Transcription based amplification reactions may also be performed with thermostable enzymes. Transcription based amplifications are usually carried out at a temperature around 41 degrees Celsius. Thermostable enzymes allow the reaction to be carried out at more elevated temperatures. Such a thermostable method is described in EP 682121 filed in the name of Toyo Boseki K K.

The methods as described in EP 323822, EP 373960 and EP 408295 are isothermal continuous methods. With these methods four enzyme activities are required to achieve amplification: an RNA dependent DNA polymerase activity, a DNA dependent DNA polymerase activity, an RNase (H) activity and an RNA polymerase activity. Some of these activities can be combined in one enzyme, so usually only 2 or 3 enzymes are necessary. Reverse transcriptase such as AMV (Avian Myoblastosis Virus) or MMLV (Moloney Murine Leukemia Virus) reverse transcriptase have both RNA- and DNA dependent DNA polymerase activity but also an inherent RNase H activity. In addition an RNase may be added to the reaction mixture of a transcription based amplification reaction, such as E. coli RNase H. DNA dependent RNA polymerases synthesize multiple RNA copies from a DNA template including a promoter recognized by the RNA polymerase. Examples of RNA polymerases are polymerases from E. coli and bacteriophages T7, T3 and SP6. An example of an RNA polymerase commonly used with transcription based amplification methods is T7 polymerase. Thus the promoter that is incorporated in the template used to produce multiple copies of RNA would then be the T7-promoter. Usually the template comprising the promoter has to be created starting from the nucleic acid comprising the target sequence. Said nucleic acid may be present in the starting material that is used as input for the amplification reaction. The nucleic acid present in the starting material will usually contain the target sequence as part of a much longer sequence. Additional nucleic acid sequences may be present on both the 3'- and the 5'-end of the target sequence. The amplification reaction can be started by bringing together this nucleic acid from the starting material, the appropriate enzymes that together provide the above mentioned activities and at least one, but usually two, oligonucleotide(s). At least one of these oligonucleotides should comprise the sequence of the RNA polymerase promoter.

Transcription based amplification methods are particularly useful if the input material is single stranded RNA, although single or double stranded DNA can likewise be used as input material. When a transcription based amplification method is practiced on a sample with single stranded RNA with additional sequences on both the 3'-end and the 5' end of the target sequence a pair of oligonucleotides that is conveniently used with the methods as described in the prior art would consist of:
  a first oligonucleotide (usually referred to as "promoter-primer" or "forward-primer") that is capable of hybridizing to the 3'-end of the target sequence, which oligonucleotide has the sequence of a promoter (preferably the T7 promoter) attached to its 5' end (the hybridizing part of this oligonucleotide has the opposite polarity as the target RNA used as input material).
  a second oligonucleotide (usually referred to as "reverse primer") which comprises the 5' end of the target sequence (this oligonucleotide has the same polarity as the target RNA).

When such a pair of oligonucleotides, together with all enzymes having the appropriate activities, and a sufficient supply of the necessary ribonucleotides and deoxy-ribonucleotides are put together in one reaction mixture and are kept under the appropriate conditions (that is, under the appropriate buffer conditions and at the appropriate temperature) for a sufficient period of time an isothermal continuous amplification reaction will start. Many variants of the above theme have been described in the prior art. A transcription based amplification reaction comprises the synthesis of single stranded RNA transcripts from a template comprising a promoter (e.g. the T7 promoter) that is recognized by an RNA polymerase (e.g. T7 RNA polymerase). A forward primer, comprising the promoter sequence, serves as a primer to initiate the synthesis of a strand of DNA complementary to the target RNA.

The primer will be extended by the activity of RNA dependent DNA polymerase. The RNA-cDNA hybrid formed will be degraded by RNase H. This enables the hybridization of the specific reverse primer to the cDNA. Extension of this primer by RNA dependent DNA polymerase up to the 5' end of the cDNA results in the formation of a double-stranded promoter sequence, whereby the promoter sequence that was part of the forward primer is used as a template. This double stranded promoter will then be used by the DNA dependent RNA polymerase to produce many new RNA molecules that are complementary to the target RNA. After this initiation phase, the amplification enters a cyclic phase.

In practice, the whole sequence of events, starting from the single stranded RNA in the sample, will take place as soon as all ingredients are put together, and the mixture is brought to the appropriate temperature for the enzymes to be all active. The practitioner of the method need not to intervene to accomplish any of these steps.

As explained above, transcription based amplification methods are particularly useful for amplifications that start from single stranded RNA. The starting material containing the nucleic acid to be amplified may not contain the target nucleic acid as RNA of a defined length. When a transcription based amplification method is performed on starting material comprising the target sequence only as double stranded DNA, either circular or linear, the DNA would have to be converted to single stranded nucleic acid. This can be achieved by separating the strands of the double stranded DNA by applying an elevated temperature (up to a 100 degrees Celsius). The first of the oligonucleotides used as primers in the amplification may than anneal to one of the single strands. The enzymes used with current transcription based amplification methods cannot withstand such a high temperature and consequently can only be added after the DNA strands have been separated. When one of the oligonucleotides anneals to a single strand DNA and is elongated, double stranded DNA is created again, and the reaction mixture would have to be subjected to an elevated temperature sufficiently high to melt the double stranded DNA into its separated strands again. Again the enzymes would be inactivated and new enzymes are to be added after the heat step has been applied. The second oligonucleotide can now be added and anneal to the strand that was created from the elongated first oligonucleotide in the first step. As one of the oligonucleotides includes a 5' promoter sequence of a DNA dependent RNA polymerase (see above), a double stranded DNA template including a double stranded functional promoter is obtained, from which a first step of RNA production can take place. The resulting RNA transcripts may enter the cyclic phase of the amplification and the process can further be isothermal.

From the above it is evident that starting a transcription based amplification method from double stranded DNA can be a tedious process. It requires several specific actions to be taken by the practitioner; the sample has to be heated and cooled repeatedly and enzymes have to be replenished after each heating step.

Some research has already gone into the developments of transcription based amplification methods that can start from dsDNA, avoiding the tedious procedure described above to convert the dsDNA into ssRNA that can be used as input for the cyclic isothermal transcription based amplification.

A rather simple transcription based amplification method for dsDNA has been disclosed in WO9925868.

According to the method described in WO9925868 dsDNA in a sample can be amplified by means of a transcription based amplification protocol directly, without any heat treatment step [of over 90 C] at all, or—in a preferred embodiment—with only one initial heating step. dsDNA, that is relatively short, is to be preferred in this method. Actually, the method does not differ essentially from a conventional transcription based amplification protocol to amplify ssRNA.

Alternatively, the double stranded DNA in the starting material can be transcribed into RNA before the start of the amplification. Such an extra step can be based on an enzyme, for instance E. coli RNA polymerase, that transcribes the double stranded DNA into RNA without the presence of a promoter sequence, also referred to as a polymerase binding site. Such a process of extra steps to facilitate the amplification of double stranded DNA by transcription based amplification methods has been described in PCT patent application no. WO9602668. The extra steps described in this procedure do not only include extra handling steps and handling time, but also the use of additional ingredients, i.e. the E. coli RNA polymerase.

Another way of preparing suitable templates for transcription based amplification methods for dsDNA is described in EP 397269.

In this patent a method is described whereby dsDNA is pretreated with a restriction enzyme. After treatment with the restriction enzyme only one heat separation step is needed to create single stranded DNA (ssDNA). With this method a forward primer (promoter-primer) is used that has a 3' part including a sequence that is complementary to the exact 3' end of one of the single strands of DNA and a 5' end including a promoter sequence recognized by a RNA polymerase (for example T7 RNA polymerase). When the promoter-primer is hybridized to the 3' end of the single strand of DNA a double stranded complex is formed, of which the 5' promoter sequence of the forward primer can serve as a template for an elongation reaction starting from the 3' end of the DNA strand. Thus, a double stranded promoter is formed by a DNA dependent DNA polymerase and the resulting complex can serve as template for the DNA dependent RNA polymerase to synthesize multiple copies of RNA.

In WO9104340 also several methods are disclosed to start a transcription based amplification reaction for single stranded DNA. Again, a restriction enzyme may be used to create an appropriate 3' end on the DNA, which can hybridize with a 3' sequence of a promoter primer.

In WO9104340 it is disclosed how the defined 3' end on the ssDNA may be created using a restriction enzyme that cuts ssDNA. In another embodiment of the same method, a restriction enzyme is used that cuts dsDNA, together with a restriction oligonucleotide that hybridizes to the target ssDNA and thus creates a double stranded piece of DNA that can be cut by the restriction enzyme to create the appropriate 3' end. With this method a small piece of the restriction oligonucleotide will remain after the restriction enzyme has cut the double stranded complex. However, according to the disclosure of WO9104340, the restriction oligonucleotide is apparently chosen in such a way that after digestion, the remaining piece will be too small to stay hybridized to the 3' end of the ssDNA, and thus will fall of to make room for the promoter oligonucleotide. However, the pre-treatment with a restriction enzyme as used with the prior art methods, although it may result in a sensitive transcription based assay, require many extra handling steps and handling time.

Hepatitis B virus (HBV) infection in humans is widespread. The virus that causes hepatitis B appears to infect only humans and chimpanzees.

The hepatitis infection is transmitted by three general mechanisms: (1) by parenteral inoculation of infected blood or body fluids, either in large amounts as in blood transfusions or in minute amounts as through an accidental skinprick; (2) by close family or sexual contact; and (3) by some mothers, who transmit the virus to their new-born children. Under natural conditions, HBV is not highly contagious. Transmission by inhalation occurs rarely, if ever. The transmission route through contaminated blood or blood products is a major threat to the human health.

Infection with HBV often results in subclinical or acute self-limited liver disease or can result in chronic long-term infection. Chronic HBV infection elicits a spectrum of disease entities ranging from the most severe form of chronic active hepatitis to less severe chronic persistent hepatitis to the asymptomatic carrier state. An array of diagnostic assays has recently been developed to aid the clinician in differentiating hepatitis B virus infections from other forms of viral hepatitis (i.e., hepatitis A, hepatitis C or hepatitis E). However, the ability to distinguish between an acute hepatitis B infection and symptomatic chronic hepatitis B infection is still problematic. This is especially true since chronic active hepatitis and chronic persistent hepatitis patients often demonstrate a cyclic pattern of hepatitis characterized by acute exacerbation of liver injury alternating with normal liver function.

After infection with HBV, large quantities of the virus and associated particles are present in the serum. During symptomatic phases of infection, both acute and chronic HBV patients have elevated liver enzyme levels, possess the hepatitis B surface antigen (HBsAg) in their serum, and produce antibodies to the nucleocapsid antigen (HBcAg). Antibodies specific for the HBsAg or the hepatitis B e antigen (HBeAg) are not detected. The appearance of antibody to HBsAg is usually not observed until approximately two months following disappearance of circulating HBsAg. The viral particles present in the serum are known to shed their surface coat exposing the nucleocapsid, known as the core antigen (HBcAg). Antibody production of HBcAg occurs early in the course of the acute phase of HBV infection and can persist for many years, and chronically infected patients can produce high titers of anti-HBc antibodies.

HBsAg is established as the most important marker of acute or chronic hepatitis B infection, detectable in serum of infected individuals. HBsAg screening of donor blood for example, is essential to avoid transmission of hepatitis B. It is clear that sensitivity is of utmost importance in diagnostic HBV assays.

HBV is the smallest DNA virus known, and its genome shows a highly compacted organization. A unique aspect in the replication cycle of HBV is that a pre-genomic mRNA serves as a template for the synthesis of the first viral DNA strand. The RNAse H activity of the HBV DNA polymerase subsequently removes the mRNA and the complementary DNA strand is then synthesized, generating a partially double stranded DNA molecule for packaging in virions. Upon successful virus entry, the partially double stranded DNA molecule is converted into a fully double stranded DNA molecule.

HBV DNA can be detected in the blood of infected hosts who are HBsAg and HBeAg positive in more than 90% of cases. The state of the art method of measuring the quantity of infectious particles is by measuring the quantity of viral DNA in serum or plasma, because it most reliably reflects the amount of replicating virus. Several assays are available for this purpose, such as the branched DNA (bDNA) assay (Hendricks D A, Stowe B J, Hoo B S, Kolberg J, Irvine B D, Neuwald P D, Urdea M S, Perrillo R P, 1995. Quantitation of HBV DNA in human serum using a branched DNA (bDNA) signal amplification assay. *Am J Clin Pathol* 104: 537-546), DNA hybridization assays and quantitative PCR (Pawlotsky J M, Bastie A, Lonjon I, Remire J, parthuy F, Soussy C J, Dhumeaux D, 1997. What technique should be used for routine detection and quantification of HBV DNA in clinical samples? *Journal of Virological Methods* 65: 245-253. Zaaijer H L, ter Borg F, Cuypers H T, Hermus M C, Lelie P N, 1994. Comparison of methods for detection of hepatitis B virus DNA. *J Clin Microbiol* 32: 2088-2091). Most of these assays, however, have only limited sensitivity.

The present invention is concerned with a transcription based amplification method including a restriction enzyme digestion. The method enables a sensitive and specific amplification (and subsequent detection) of DNA of the Hepatitis B virus. With the method of the invention HBV DNA can be amplified and detected in a more efficient way than with prior art transcription based amplification methods In contrast to the prior art methods the use of the restriction enzyme does not complicate the procedures used method of the invention.

The present invention provides a method for the transcription based amplification of a target HBV nucleic acid sequence starting from HBV DNA optionally present in a sample, comprising the steps of:

incubating the sample, suspected to contain HBV, in an amplification buffer with one or more restriction enzymes capable of cleaving the DNA at a selected restriction site, said restriction enzyme creating a defined 3' end on one of the DNA strands, and a promoter-primer, said promoter-primer having a 5' region comprising the sequence of a promoter recognized by a DNA-dependent RNA polymerase and a 3' region complementary to the defined 3' end of the DNA strand, a second primer, having the opposite polarity of the promoter-primer and comprising the 5' end of the target sequence, and in case of a HBV ssDNA, a restriction primer,
maintaining the thus created reaction mixture under the appropriate conditions for a sufficient amount of time for a digestion by the restriction enzyme to take place,
subjecting the sample to a heat treatment at a temperature and time sufficient to inactivate the restriction enzyme and/or to render at least partially a double strand single stranded,
adding the following reagents to the sample:
an enzyme having RNA dependent DNA polymerase activity
an enzyme having DNA dependent DNA polymerase activity
an enzyme having RNase H activity
an enzyme having RNA polymerase activity, and
maintaining the thus created reaction mixture under the appropriate conditions for a sufficient amount of time for the amplification to take place.

The [for an adequate amplification] necessary (appropriate) nucleoside triphosphates may be present already during the incubation step with the restriction enzyme(s), for example as part of the said amplification buffer. They may, however, be added later on in the process, for example together with the enzymes after the heat treatment.

The person skilled in the art knows the enzymes used for the transcription based amplification method, and the conditions under which the transcription based amplification method is carried out and is aware of all the usual modifications that can be made with regard to optimizing transcription based amplification reactions. For example, the forward primer, the promoter primer, may comprise a purine region between the promoter sequence on the 5' end of the primer and the hybridizing sequence on the 3' end of the primer.

The sequence of the primers is largely determined by the position of the restriction site chosen.

The 3' end of a forward primer should anneal to the target sequence directly next to the restriction site. The primer may vary in length as long as it is sufficiently long to hybridize under the conditions used with the amplification reaction. In general the hybridizing part of the primer consists of about 10 to about 35 nucleotides.

Restriction primers, used in the method according to the invention if the target is HBV ssDNA, require that the overlap they show with the forward primer is minimal and the sequence of the restriction site is incorporated in such a way that the restriction enzyme actually cuts the DNA efficiently.

A restriction enzyme is an enzyme that can cut dsDNA at a selected site (i.e. a specific nucleotide sequence recognized by the enzyme). In selecting an appropriate restriction enzyme for the method of the invention care should be taken that a restriction site is chosen that is present in al variants of the HBV DNA (for example, a restriction site that is present in all genotypes of the hepatitis B virus, if the amplification is carried out to detect all viral HBV DNA in the sample). The restriction site should not be present in the DNA sequence in between the forward and reverse primers used.

The addition of the restriction enzyme results in the creation of a defined 3' end of the target strand of the DNA, which is then available for binding to the hybridizing part of the promoter primer. An additional aspect is that, because of the digestion, denaturation of that part of the DNA will be improved and so primer binding will be facilitated.

The promoter oligonucleotide containing the T7-promoter sequence should be designed in such a way that the hybridizing part will interact with the template directly upstream of the restriction site. The enzyme having DNA dependent DNA polymerase activity (usually a reverse transcriptase such as MMLV-RT or AMV-RT) can extend the 3' end of the target strand of the DNA created by the digestion with the restriction enzyme, using the primer as template. A double-stranded T7-promoter sequence will be formed and the production of amplicon RNA can start.

Surprisingly it has been found that a restriction enzyme can be used efficiently in an environment that is suitable for and adapted to a transcription based HBV DNA amplification process. In other words it has been found that the use of a restriction enzyme to cut the HBV DNA that is used as input material for a transcription based amplification, does not have to lead to complicated, additional handling of the sample. The use of the restriction enzyme is incorporated into and is part of the steps that are usually already part of the protocol for a transcription based DNA amplification.

All prior art methods describe the use of a restriction enzyme in the preparation of a DNA template for transcription based amplification as a separate pre-treatment prior to the actual transcription based amplification. Consequently the prior art use of a restriction enzyme in preparing the DNA template resulted in additional handling of the sample, like separate inactivation of the restriction enzyme and separate purification of the DNA. It complicates the whole amplification procedure, especially an automated process, and increases the risk of contamination.

Although the addition of a restriction oligonucleotide together with a restriction enzyme has already been disclosed in WO9104340, it has not been disclosed prior to the present invention how the use of the restriction enzyme (and oligonucleotide) can efficiently be combined with the transcription based amplification.

It has not been disclosed in the prior art in which way the use of restriction enzyme can be combined with transcription based amplification without additional sample handling and reagent adding steps.

The method of the invention provides this combination without complicating the prior art transcription based DNA amplification process.

The method of the invention hardly differs from a normal transcription based amplification method. The only additional step to be taken is the "built in incubation" of the sample with the restriction enzyme, which means that the restriction enzyme is used in such a way that the actual handling of the sample does not differ from a conventional/prior art transcription based DNA amplification process.

The preferred restriction enzyme used in the method of the invention is, of course, an enzyme that is relatively stable and retains a high activity under conditions where it is added to a reaction mixture comprising an amplification-buffer (which contains relatively high concentrations of salts).

After the addition of the restriction enzyme the sample needs to be incubated under the appropriate conditions for the enzyme to be active, and for a suitable amount of time. The sample may be incubated with the restriction enzyme for a relatively short period of time, preferably for about 10-20 minutes and more preferred for about 15 minutes at a temperature of about 35 to about 45° C. and more specifically at about 37-41° C., obviously depending on the nature of the restriction enzyme used. In fact, this is the only additional measure to be taken, when compared to a conventional transcription based DNA amplification method.

The method of the invention comprises the step of heating the sample after the incubation with the restriction enzyme. During this heating the restriction enzyme is inactivated and double stranded DNA is rendered single stranded [at least partially]. This heating step is already part of the protocols for carrying out a transcription based amplification method. These methods involve a heat treatment of the sample after primer-addition, to create optimal circumstances for primer annealing (the nucleic acid is stretched, strands or internal loops of the nucleic acid are separated, and during the cooling down, hybridization of the primers to the template is facilitated.)

The heating after the incubation with the enzyme may be done at a lower temperature of about 50° C. or higher, but is preferably carried out by way of a short incubation (about 5-10 minutes) at a temperature above 90° C. and preferably at 95+/−3° C.

Thereafter the sample may be cooled to the appropriate temperature for a transcription based amplification reaction to take place (usually about 41° C.).

Due to the heating, at least a part of the double stranded DNA is rendered single stranded. As the primers, especially the promoter oligonucleotide, are already present prior to the heating of the sample, the heat treatment may facilitate primer annealing to DNA as well.

Thus, there is no need to purify the DNA from the sample after it has been subjected to a treatment with the restriction enzyme. The enzyme is simply inactivated in the heat treatment that was already part of the transcription based amplification procedure. It has been proven with the method of the invention that this is sufficient to eliminate the risk that the restriction enzyme will interfere with the actual transcription based amplification reaction.

After the heat treatment the additional amplification reagents for the transcription-based amplification are added in the usual way, and the transcription based amplification can be carried out in the usual way known to the skilled person The amplification enzymes are only added after the heat treatment, to prevent degradation of the enzymes during the heat treatment (unless, of course, thermostable enzymes are used).

The major advantage of the method of the invention is that, even though that additional reagents are used (e.g. the restriction enzyme) this does not result in additional (separate) reaction steps or activities to be carried out.

The fact that no additional handling of the sample is required is especially important because every additional handling of the sample would increase the contamination risk, which is to be avoided at all costs, especially in amplification reactions. Moreover, if additional sample handling steps were required this would complicate automation of the method.

The method of the invention may also be used for single stranded DNA. When the DNA is single stranded a restriction oligonucleotide or restriction primer comprising a sequence complementary to the region including the restriction site of the target DNA is added together with the restriction enzyme. The restriction oligonucleotide [restriction primer] hybridizes with the single stranded DNA and forms a double stranded complex that can be cut with the restriction enzyme.

The addition of yet another reagent (the restriction oligonucleotide) does not result in additional steps to be carried out by the practitioner. The restriction oligonucleotide can simply be added together with the restriction enzyme and the other oligonucleotides necessary for the amplification. Thus, there is no need to open the amplification system for yet another addition of reagents.

In a preferred embodiment of the invention, the function of the restriction oligonucleotide may be incorporated in the oligonucleotide that also comprises the sequence of a promoter recognized by a DNA dependent RNA polymerase (the combined promoter and restriction-primer). In this way only two oligos are needed for the amplification, a promoter [or forward] primer in which a sequence complementary to the target region including the restriction site has been incorporated and the second [or reverse] primer.

The sequence including the restriction site of this preferred [combined promoter and restriction] primer should preferably be allocated in such a way that:

after digestion, the remaining part of the primer will denature from the target during the heating step the remaining part of the hybridizing sequence of the target is long enough for a new combined promoter and restriction primer to bind, Extra nucleotides surrounding the restriction site are included in the hybridization if necessary for the activity of the restriction enzyme.

Thus, a part of the combined promoter and restriction primer will now serve as restriction oligonucleotide; it will anneal to the target DNA, resulting in dsDNA comprising the restriction site recognized by the restriction enzyme. Subsequently the restriction enzyme will cut the said dsDNA, thus providing the defined 3' end on the DNA.

Preferably, an at least 1000 fold excess of this combined promoter and restriction primer with respect to the amount of target DNA should be present, as is also usual already for a conventional promoter primer in transcription based amplification reactions.

The method of the invention provides an efficient and sensitive method for the amplification and detection of viral DNA in samples suspected to contain the hepatitis B virus (HBV), especially with the HBV primers and HBV probes as described herein. Hence, these HBV primers and HBV probes represent another embodiment of the invention, The restriction site that is selected in the method of the invention is preferably one that is conserved among the different genotypes of HBV.

Good results were obtained if the target sequence and restriction site were located in the part of the HBV genome that encodes the surface antigen.

Conserved restriction sites in the HBsAg coding region that are especially useful in the method of the invention (together with the restriction enzymes that cut at these sites) are the XbaI site located at nucleotides 247-252 according to the EcoRI site, the BssSI site located at nucleotides 253-258 according to the EcoRI site and the AvrII site located at nucleotides 178-183 according to the EcoRI site.

The oligonucleotide sequence of the primers is, of course, largely determined by the position of the restriction site chosen. The primer may vary in length as long as it is sufficiently long to hybridize under the conditions used with the amplification reaction. In general the hybridizing part of the primer consists of about 10 to about 35 nucleotides and more preferably of about 15 to about 30 nucleotides.

The 5' end of a forward primer should anneal to the target sequence directly next to the restriction site.

The position of the reverse primer is less critical, preferably it should have the sequence of a part of a conserved region sufficiently remote from the position of the forward primer to allow a probe to hybridize to the amplified target sequence in the region in between the forward and reverse primer region.

The preferred restriction primer is an oligonucleotide that has a minimal overlap with the forward primer, includes the sequence of the restriction site in such a way that the restriction enzyme can actually cut the dsDNA thus formed and is sufficiently long so as to hybridize with the HBV DNA in a sufficient manner.

Oligonucleotide forward primers which are especially useful in combination with the XbaI, AvrII and/or BssSI restriction enzymes are preferred embodiments of the invention. Specifically, oligonucleotide sequences comprising at least 10 and preferably more than 15 nucleotides [counted from the cleavage site] of the HBV hybridizing part of SEQ ID No 1 [said hybridizing part as such being SEQ ID No 10] in combination with the restriction enzyme XbaI, of the HBV hybridizing part of SEQ ID No 2 [said hybridizing part as such being SEQ ID No 11] in combination with BssSI and/or of the hybridizing part of SEQ ID No 3 [said hybridizing part as such being SEQ ID No 12] in combination with AvrII are preferred.

Oligonucleotides which can be used as restriction primers, comprise at least 10 and preferably more than 15 nucleotides "flanking" the HBV DNA restriction site concerned and especially "flanking" the XbaI site located at nucleotides 247-252 according to the EcoRI site, the BssSI site located at nucleotides 253-258 according to the EcoRI site and the AvrII site located at nucleotides 178-183 according to the EcoRI site.

Particularly suitable restriction primers have the oligonucleotide sequences depicted in SEQ ID No. 8 and SEQ ID No 9.

Suitable probes for the detection of the amplified HBV target contain from 10 to about 35 and more preferably from about 15 to about 30 nucleotides which hybridize with the amplified HBV target and comprise at least 10 and preferably more than 15 nucleotides of the HBV hybridizing part of SEQ ID No 6 and SEQ ID No 7. (The HBV hybridizing parts of these sequences are shown in Table 1 and indicated as SEQ ID No 13 and SEQ ID No 14 respectively. The probes shown in Table 1 are further provided at both ends with non-HBV nucleotides forming entirely or sometimes together with a few HBV nucleotides the "stem" of the probe; said stem being part of the detection system chosen).

Suitable reverse primers contain from about 10 to about 35 and more preferably from about 15 to about 30 nucleotides of a conserved region of HBV. Preferred reverse primers comprise at least 10 and preferably more than 15 nucleotides of SEQ ID No 4 and SEQ ID No 5.

Another embodiment of the invention is a test kit suitable for carrying out the transcription based amplification and detection of HBV DNA according to the invention comprising:

a restriction enzyme as herein described, a forward primer that corresponds with the cleavage site of the restriction enzyme chosen, as herein explained, and is provided with a promoter sequence, other reagents for carrying out a transcription based amplification reaction, means for detecting the amplified HBV DNA, and instructions for use.

BRIEF DESCRIPTION OF THE FIGURES

FIG. 1: Schematic presentation of DNA NASBA including restriction enzyme digestion. The restriction enzyme (arrow) is only active during the initiation phase of NASBA. After digestion, the forward primer is hybridized to the template. AMV RT will extend the 3' end of the target strand (black) of the DNA, using the forward primer, including the T7 promoter sequence (dark grey) as template. The T7 DdRp will recognize the double stranded T7 promoter sequence and RNA amplicon (light grey) production will begin. The RNA amplicon sequence is complementary to the target DNA strand. During the cyclic phase, the RNA amplicon will be amplified and detected by molecular beacon technology. RNase H and the reverse primer are only required during the cyclic phase.

The invention is further exemplified by the following Examples.

EXAMPLES

Example 1

Amplification of HBV DNA

Two conserved restriction sites (XbaI and BssSI) are encoded in the conserved region (nt 244 to 285 according to the EcoRI-site) of the S-gen of HBV DNA. As this part of the S-region can be single-stranded DNA of negative polarity, an oligonucleotide ('restriction primer' (RP) complementary to the region including the restriction site sequences was added to create a double-stranded restriction site for all genomic DNAs present. HBV DNA was isolated from a series of dilution of plasma infected with HBV genotype A of $3 \times 10^9$ geq/ml, using the Nuclisens Extractor (Organon Teknika). Following the standard procedure as described for RNA isolation (Operator Manual Extractor, 41001-9, rev A, 1999), a 50 μl extract is obtained. Five μl of the extract is used per assay. The restriction enzyme digestion was performed in NASBA buffer (40 mM Tris-HCl pH 8.5, 12 mM $MgCl_2$, 70 mM KCl, 15% v/v DMSO, 5 mM DTT, 1 mM each dNTP, 2 mM ATP, 2 mM CTP, 2 mM UTP, 1.5 mM GTP, 0.5 mM ITP, 0.2 μM forward primer (S-p3.8 for XbaI, and S-p3.10 for BssSI, table 1), 0.2 μM reverse primer (S-p4.5, table 1), 0.1 μM molecular beacon probe (S-WT2, table 1), 0.17 μM restriction primer (RP-3, table 1)) and 0.2 units restriction enzyme BssSI (New England BioLabs, Inc., Beverly, Mass., USA) or 3.0 units restriction enzyme XbaI (New England BioLabs, Inc., Beverly, Mass., USA). After incubation of 15 min at 41° C., the restriction enzymes were heat-inactivated and the DNA template denatured at 95° C. for 5 min. Hybridization of the primers occurred during cooling down to 41° C. for 3 min. Subsequently, NASBA enzymes (2.1 μg BSA, 0.08 units RNase H, 32 units T7 RNA polymerase and 6.4 units AMV reverse transcriptase) were added, the reaction mixture was mixed by gently tapping and short centrifugation, and the amplification and real-time detection was started. The reaction mixture was incubated at 41° C. in the NucliSens EasyQ Analyzer (Organon Teknika) for 120 minutes with fluorescence monitoring every minute. The reactions were excited at 485 nm and the emission signal was measured at 518 nm.

Example 1.1

Amplification of HBV DNA Including XbaI Digestion

Figure 1:
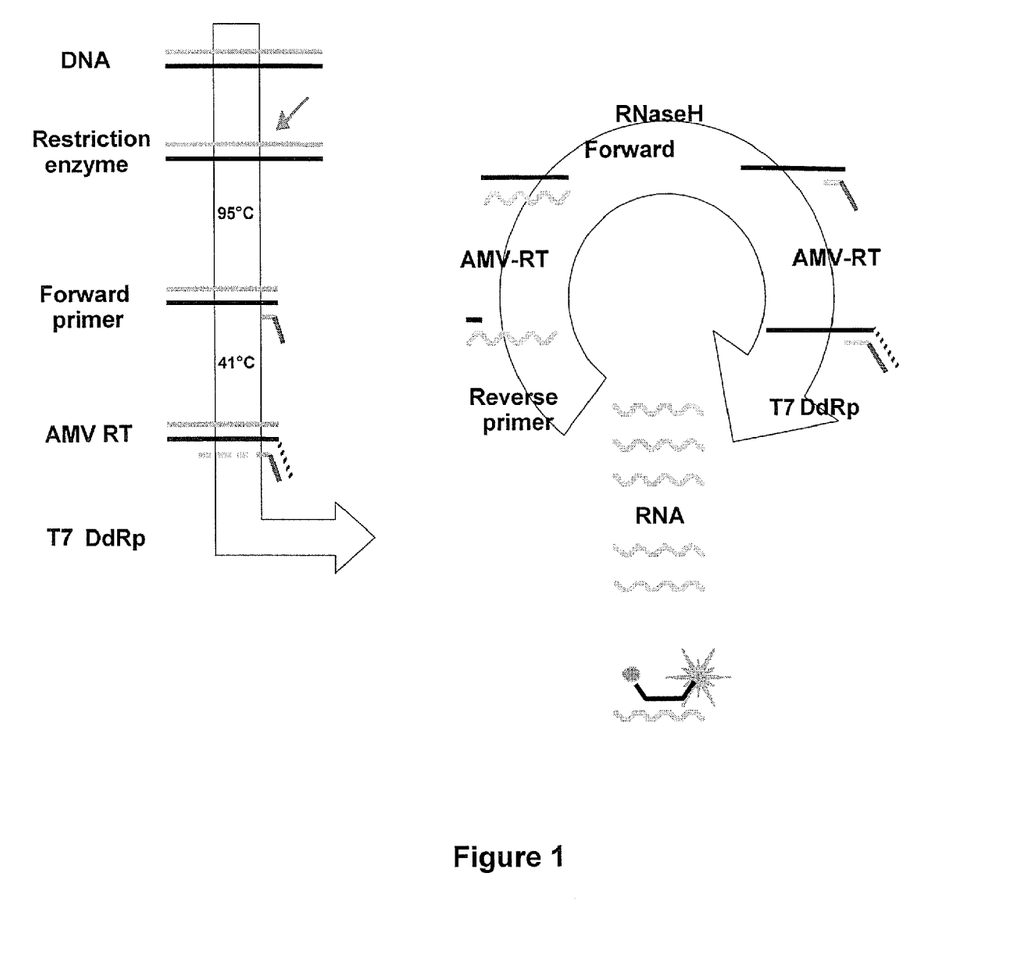
Figure 2:
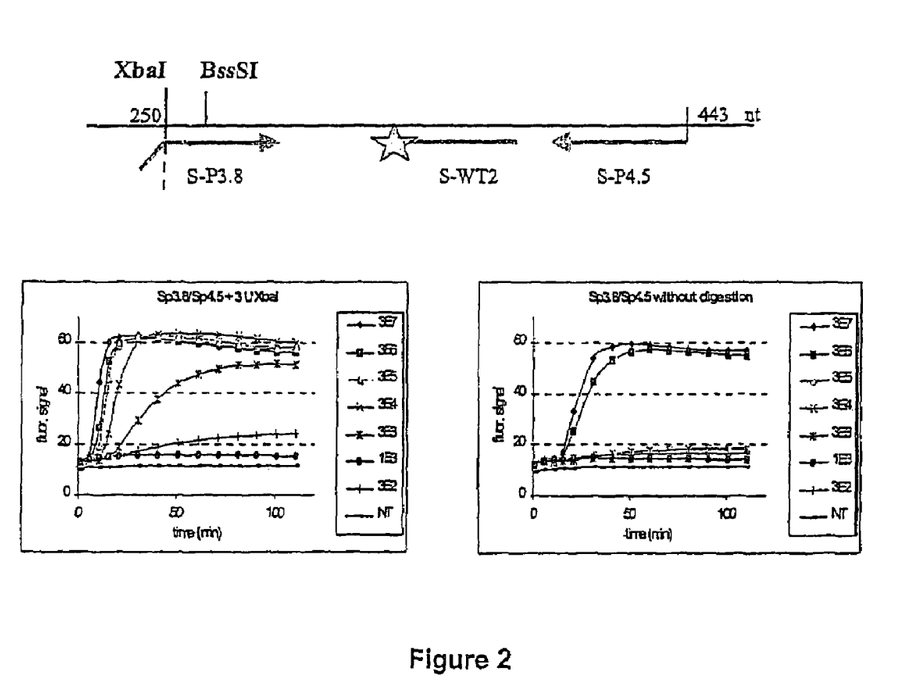
FIG. 2: NASBA of HBV DNA with and without digestion with XbaI in combination with forward primer S-p3.8. After digestion with XbaI, S-p3.8 can be used as template for the extension of target DNA. Primer S-p4.5 is used as reverse primer and molecular beacon S-WT2 as probe. A sample without template (NT) is used as negative control.

A NASBA assay with and without the treatment with the restriction enzyme XbaI was performed. The optimal concentration of XbaI was determined under NASBA conditions by digestion of $10^9$ copies of a PCR fragment including the amplicon region of the HBV DNA, and was shown to be 3 units. S-p3.8 is used as forward primer and can be used as template by AMV RT to extend the template DNA after digestion with XbaI. Without digestion a sensitivity of $3 \times 10^6$ geq/ml is obtained while after digestion the sensitivity is $3 \times 10^3$ geq/ml, meaning a 1000 fold increase in sensitivity (FIG. 2). In addition, without digestion the time to positivity (TTP) is about 16 minutes while after XbaI digestion this is about 6 min, meaning a decrease in TTP of about 10 min (FIG. 2). Both are indications for an improved amplification reaction.

Example 1.2

Amplification of HBV DNA Including BssSI Digestion

Figure 3:
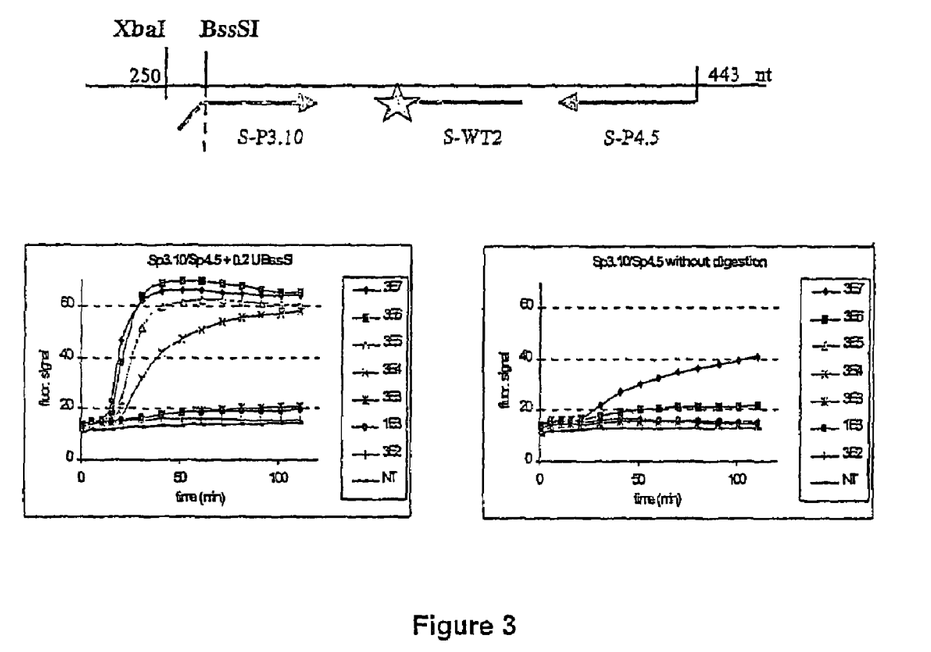
FIG. 3: NASBA of HBV DNA with and without digestion with BssSI in combination with forward primer S-p3.10. After digestion with BssSI, S-p3.10 can be used as template for the extension of target DNA. Primer S-p4.5 is used as reverse primer and molecular beacon S-WT2 as probe. A sample without template (NT) is used as negative control.

A NASBA reaction, with and without treatment with the restriction enzyme BssSI was performed with the same HBV DNA extract and comparable reaction conditions as described above. The optimal concentration of BssSI was determined under NASBA conditions by digestion of $10^9$ copies of a PCR fragment including the amplicon region of the HBV DNA, and was shown to be 0.2 units. S-p3.10 is used as forward primer and can be used as template by AMV RT to extend the template DNA after digestion with BssSI. Again significant test improvements were obtained as a result of treatment with the restriction enzyme BssSI (FIG. 3). Without digestion a sensitivity of only $3\times10^7$ geq/ml is obtained while after digestion the sensitivity is $3\times10^4$ geq/ml, meaning again a 1000 fold increase in sensitivity (FIG. 3) as a result of the digestion. In addition, without digestion the time to positivity (TTP) is about 21 minutes while after BssSI digestion this is about 11 min, meaning again a decrease in TTP of about 10 min (FIG. 3). The results prove that the digestion of HBV DNA with a restriction enzyme prior to the NASBA reaction can considerably improve the amplification and so the detection of a HBV DNA Example 1.3

Amplification of HBV DNA Including XbaI Digestion-2

Figure 4:
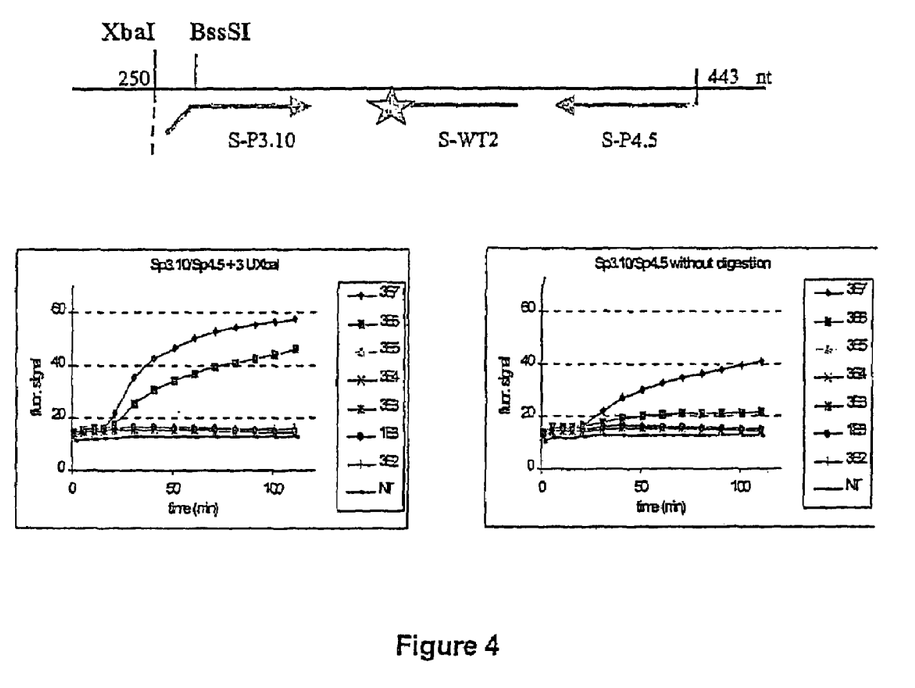
FIG. 4. NASBA of HBV DNA with and without digestion with XbaI in combination with forward primer S-p3.10. S-p3.10 can not be used as template for the extension of target DNA, after digestion with XbaI. Primer S-p4.5 is used as reverse primer and molecular beacon S-WT2 as probe. A sample without template (NT) is used as negative control.

To test if the digestion by itself or the combination of the restriction enzymes with the selected primers was the basis for the improved assay results, the assay including the XbaI digestion was repeated with primer S-p3.10 instead of S-p3.8. AMV RT can not use S-p3.10 as template to extend the target sequence after digestion with XbaI. As can be seen in FIG. 4, only a slight increase in sensitivity (10 fold) and small decrease in TTP (about 5 min, from 21 to 16 min) is obtained after digestion with XbaI in combination with S-p3.10. This indicates that the extension of the template during the initiation of NASBA is responsible for the improved results as obtained with XbaI and primer S-p3.8 and with BssSI and primer S-p3.10.

Example 1.4

Amplification of HBV DNA Including BssSI Digestion-2

Figure 5:
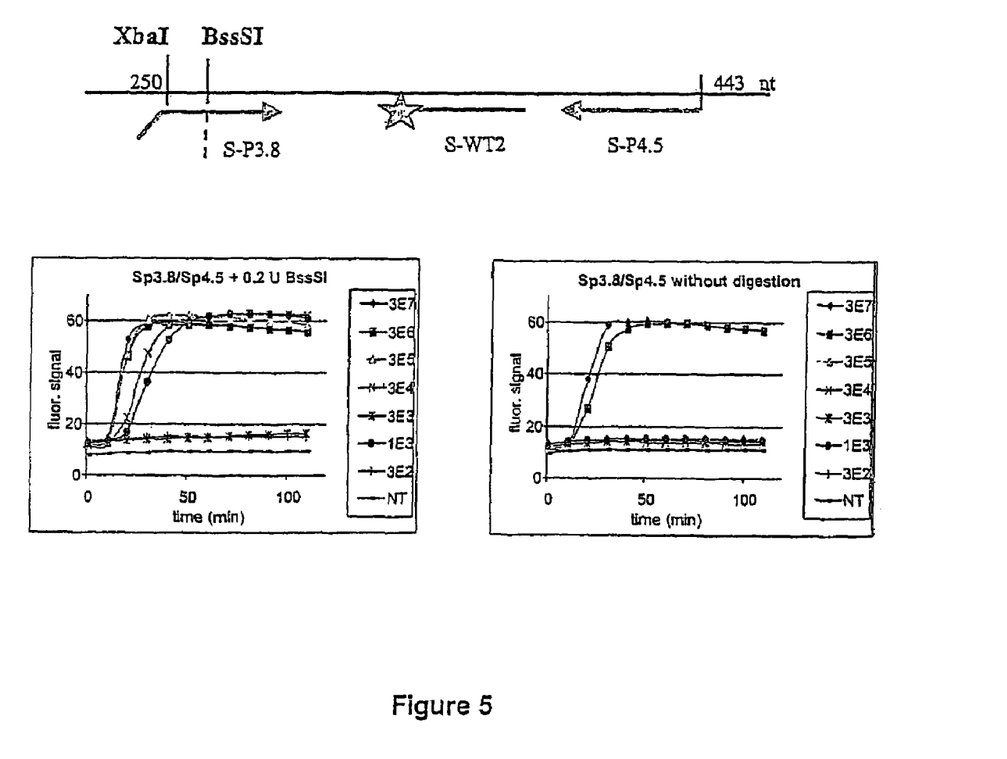
FIG. 5. NASBA of HBV DNA with and without digestion with BssSI in combination with forward primer S-p3.8. S-p3.8 can be used as template for the extension of target DNA, after digestion with BssSI. Primer S-p4.5 is used as reverse primer and molecular beacon S-WT2 as probe. A sample without template (NT) is used as negative control.

To test if the extension of the target was indeed the basis for the improved assay results, the assay including the BssSI digestion was repeated with primer S-p3.8 instead of S-p3.10. AMV RT can use S-p3.8 as template to extend the target sequence after digestion with BssSI. However, after digestion with BssSI, only 17 nucleotides are included in hybridization of the primer to the target sequence while normally this is about 20 nucleotides. Despite this difference, again clear test improvements were obtained after digestion with BssSI (FIG. 5). A double digestion can be performed with both XbaI and BssSI included in NASBA using the primers S-p3.8 and S-p4.5, restriction primer RT-3 and molecular beacon S-WT2 without loss of amplification efficiency as compared to the single digestion NASBA assays.

Example 1.5

Amplification of HBV DNA Including AvrII Digestion

Figure 6:
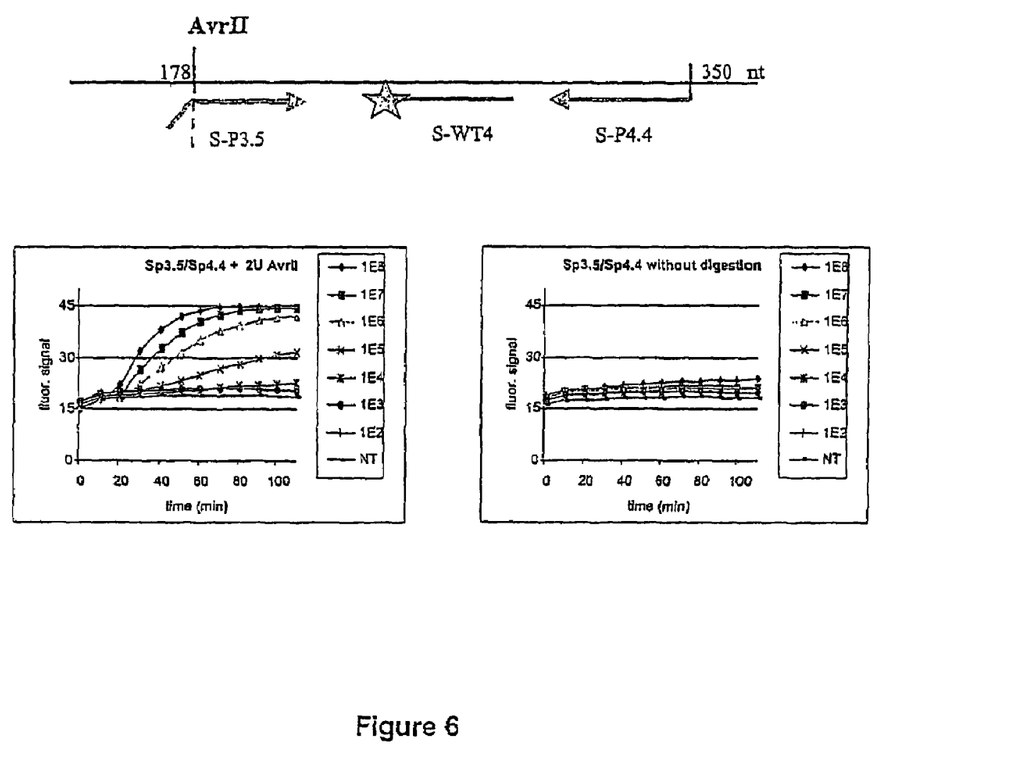
FIG. 6. NASBA of HBV DNA with and without digestion with AvrII in combination with forward primer S-p3.5. S-p3.5 can be used as template for the extension of target DNA, after digestion with AvrII. Primer S-p4.4 is used as reverse primer and molecular beacon S-WT4 as probe. A sample without template (NT) is used as negative control.

The restriction site (AvrII) is encoded in another conserved region (nt 177 to 192 according to the EcoRI-site) of the S-gen of HBV DNA. Forward primer S-p3.5, reverse primer S-p4.4, molecular beacon S-WT4 and restriction primer RP-1 (table 1) were as used in NASBA. The AMV RT can extend the target strand of HBV DNA after digestion with AvrII, using S-p3.5 as template. The same reaction conditions as described above were used. A NASBA reaction, with and without treatment with the restriction enzyme AvrII was performed with the same HBV DNA extract as described above, using 2 units of AvrII per reaction. Without digestion, a sensitivity of $>10^8$ geq/ml is obtained while after digestion the sensitivity is $1\times10^5$ geq/ml, meaning a $>10^3$ fold increase in sensitivity (FIG. 6) as a result of the digestion. Again, these results prove that the digestion of HBV DNA with a restriction enzyme digestion included in the NASBA reaction can considerably improve the amplification of HBV DNA.

TABLE 1

Primer and probe sequences

| Primer/Probe | Sequence | Label |
|---|---|---|
| S-p3.8 (SEQ ID No. 1) | 5'*AATTCTAATACGACTCACTATAGGG* a GACTCGTGGTGGACTTCTCTCA 3' | |
| S-p3.10 (SEQ ID No. 2) | 5'*AATTCTAATACGACTCACTATAGGG* agaa GGTGGACTTCTCTCAATTTTC 3' | |
| S-p3.5 (SEQ ID No. 3) | 5'*AATTCTAATACGACTCACTATAGGG* aga GGACCCCTGCTCGTGTTACAGGC 3' | |
| S-p4.5 (SEQ ID No. 4) | 5'GAACCAACAAGAAGATGAGGCA 3' | |

TABLE 1-continued

Primer and probe sequences

| Primer/Probe | Sequence | Label |
|---|---|---|
| S-p4.4 (SEQ ID No. 5) | 5'GGGACTGCGAATTTTGGCCA 3' | |
| S-WT2 (SEQ ID No. 6) | 5'<u>CGATCG</u> AGGGACTGCGAATTTTGGC <u>CGATCG</u> 3' | FAM |
| S-WT4 (SEQ ID No. 7) | 5'<u>GGATCCC</u> TIGAAAATTGAGAGAAGTCCACCAC <u>GGGATCC</u> 3' | FAM |
| RP-3 (SEQ ID No. 8) | 5'AATACCGCAGAG<u>TCTAGA</u>CTCGTGG 3'<br>                  XbaI  BssSI | 3'NH2 |
| RP-1 (SEQ ID No. 9) | 5'CATCAGGAYT<u>CCTAGGA</u> 3'<br>            AvrII | 3'NH2 |

*The T7-promoter sequence is written in italics, the purine-stretch in lower case, the stem sequence of the probe in underlined italics and the restriction sites are indicated.

---

The invention claimed is:

1. A method for the transcription based amplification of a double stranded target HBV nucleic acid sequence starting from HBV DNA optionally present in a sample, said method comprising:
   a) simultaneously incubating the sample, suspected to contain HBV, in an amplification buffer, in the absence of a restriction primer, with
      i) one or more restriction enzymes capable of cleaving the HBV DNA at a selected restriction site, said restriction enzyme creating a defined 3' end of said HBV DNA strand(s),
      ii) a promoter-primer, said promoter-primer having a 5' region comprising the sequence of a promoter recognized by a DNA-dependent RNA polymerase and a 3' region complementary to the defined 3' end of the DNA strand, and
      iii) a second or reverse primer, having the opposite polarity of the promoter-primer and comprising the 5' end of said target sequence,
   b) maintaining the thus created reaction mixture of (a) under the appropriate conditions for a sufficient amount of time for a digestion by the restriction enzyme to take place;
   c) subjecting the reaction mixture of (b) to a heat treatment at a temperature and time sufficient to inactivate the restriction enzyme and/or to render at least partially a double strand single stranded;
   d) adding the following reagents to the reaction mixture of (c):
      i) an enzyme having RNA dependent DNA polymerase activity;
      ii) an enzyme having DNA dependent DNA polymerase activity;
      iii) an enzyme having Rnase H activity; and
      iv) an enzyme having RNA polymerase activity; and
   e) maintaining the reaction mixture of (d) under the appropriate conditions for a sufficient amount of time for the amplification to take place.

2. The method according to claim 1 in which nucleoside triphosphates are added to the initial incubation mixture prior to said heat treatment.

3. The method according to claim 1 in which a reverse transcriptase is used combining the activities of the enzyme having RNA dependent DNA polymerase activity and the enzyme having DNA dependent DNA polymerase activity.

4. The method according to claim 1, in which a reverse transcriptase is used, having inherent RNase H activity, replacing the enzyme having RNA dependent DNA polymerase activity, the enzyme having DNA dependent DNA activity and the enzyme having Rnase H activity.

5. The method according to claim 1, in which the incubation temperature is from about 35° C. to about 45° C.

6. The method according to claim 1 in which the heating step is carried out at a temperature between about 92° C. and about 98° C.

7. The method according to claim 1, wherein a restriction enzyme is used that cuts the HBV DNA at a site that is conserved among the different genotypes of HBV.

8. The method according to claim 1, wherein the restriction site is located in the part of the HBV genome that encodes the surface antigen.

9. The method according to claim 8, wherein the restriction site is an XbaI site located at nucleotides 247-252 according to the EcoRI site, the BssSI site located at nucleotides 253-258 according to the EcoRI site or an AvrII site located at nucleotides 178-183 according to the EcoRI site, and the restriction enzyme used is the XbaI, BssSI or AvrII restriction enzyme.

10. The method according to claim 1, wherein the promoter or forward primer is an oligonucleotide containing from about 10 to about 35 nucleotides which hybridize with the HBV target and comprising at least 10 nucleotides, counted from the cleavage site, of the nucleotide sequence of SEQ ID NO: 10 in combination with the restriction enzyme XbaI, or of SEQ ID NO:11 in combination with BssSI or of SEQ ID NO:12 in combination with AvrII, linked to a promoter sequence.

11. The method according to claim 10, wherein the promoter oligonucleotide has the nucleotide sequence of SEQ ID NO:1, SEQ ID NO:2, or SEQ ID NO:3.

12. The method according to claim 1, wherein the amplified HBV nucleic acid is detected using a hybridization probe comprising an oligonucleotide sequence containing from about 10 to about 35 nucleotides which hybridize with the amplified HBV target and comprise at least 10 nucleotides of SEQ ID NO:13 or SEQ ID NO:14.

13. The method according to claim 12, wherein the probe has the oligonucleotide sequence of SEQ ID NO:6 or SEQ ID NO:7.

14. The method according to claim 1 wherein the second or reverse primer is an oligonucleotide containing from about 10 to about 35 nucleotides and comprising at least 10 nucleotides of the nucleotide sequence of SEQ ID NO:4 or SEQ ID NO:5.

15. The method according to claim 1, wherein the incubation temperature is from about 37° C. to about 41° C.

16. The method according to claim 1, wherein the heating step is carried out at a temperature of about 95° C.

17. The method according to claim 1, wherein the promoter or forward primer is an oligonucleotide containing from about 15 to about 30 nucleotides which hybridize with the HBV target and comprising at least 15 nucleotides, counted from the cleavage site, of the nucleotide sequence of SEQ ID NO: 10 in combination with the restriction enzyme XbaI, or of SEQ ID NO: 11 in combination with BssSI or of SEQ ID NO: 12 in combination with AvrII, linked to a promoter sequence.

18. The method according to claim 1, wherein the amplified HBV nucleic acid is additionally detected using a hybridization probe comprising an oligonucleotide sequence containing from about 15 to about 30 nucleotides which hybridize with the amplified HBV target and comprise at least 15 nucleotides of SEQ ID NO: 13 or SEQ ID NO: 14.

19. The method according to claim 1, wherein the second or reverse primer is an oligonucleotide containing from about 15 to about 30 nucleotides and comprising at least 15 nucleotides of the nucleotide sequence of SEQ ID NO:4 or SEQ ID NO:5.

* * * * *

UNITED STATES PATENT AND TRADEMARK OFFICE
CERTIFICATE OF CORRECTION

| | | |
|---|---|---|
| PATENT NO. | : 7,723,078 B2 | Page 1 of 1 |
| APPLICATION NO. | : 11/956869 | |
| DATED | : May 25, 2010 | |
| INVENTOR(S) | : Dieman et al. | |

It is certified that error appears in the above-identified patent and that said Letters Patent is hereby corrected as shown below:

In the Claims:
Column 21, Claim 4, Lines 11-12: Please correct "DNA dependent DNA activity"
to read -- DNA dependent DNA polymerase activity --

Signed and Sealed this
Fifteenth Day of February, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 48
<212> TYPE: DNA
<213> ORGANISM: Artificial Sequence
<220> FEATURE:
<223> OTHER INFORMATION: Primer

<400> SEQUENCE: 1
aattctaata cgactcacta tagggagact cgtggtggac ttctctca                48

<210> SEQ ID NO 2
<211> LENGTH: 50
<212> TYPE: DNA
<213> ORGANISM: Artificial Sequence
<220> FEATURE:
<223> OTHER INFORMATION: Primer

<400> SEQUENCE: 2
aattctaata cgactcacta tagggagaag gtggacttct ctcaattttc                50

<210> SEQ ID NO 3
<211> LENGTH: 51
<212> TYPE: DNA
<213> ORGANISM: Artificial Sequence
<220> FEATURE:
<223> OTHER INFORMATION: Primer

<400> SEQUENCE: 3
aattctaata cgactcacta tagggagagg acccctgctc gtgttacagg c                51

<210> SEQ ID NO 4
<211> LENGTH: 22
<212> TYPE: DNA
<213> ORGANISM: Artificial Sequence
<220> FEATURE:
<223> OTHER INFORMATION: Primer -continued

```
<400> SEQUENCE: 4
gaaccaacaa gaagatgagg ca                                            22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gggactgcga attttggcca                                               20

<210> SEQ ID NO 6
<211> LENGTH: 31
<212> TYPE: DNA
<213> ORGANISM: Artificial Sequence
<220> FEATURE:
<223> OTHER INFORMATION: Probe

<400> SEQUENCE: 6
cgatcgaggg actgcgaatt ttggccgatc g                                  31

<210> SEQ ID NO 7
<211> LENGTH: 39
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (9)..(10)
<223> OTHER INFORMATION: n = inosine

<400> SEQUENCE: 7
ggatccctng aaaattgaga gaagtccacc acgggatcc                          39

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
aataccgcag agtctagact cgtgg                                         25

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
catcaggayt cctagga                                                  17

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gactcgtggt ggacttctct ca                                            22
```

```
<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ggtggacttc tctcaattttt c                                          21

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12 ggaccoctgc tcgtgttaca ggc                                         23

<210> SEQ ID NO 13
<211> LENGTH: 20
<212> TYPE: DNA
<213> ORGANISM: Artificial Sequence
<220> FEATURE:
<223> OTHER INFORMATION: Probe

<400> SEQUENCE: 13
agggactgcg aattttggcc                                             20

<210> SEQ ID NO 14
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (4)..(5)
<223> OTHER INFORMATION: n = inosine

<400> SEQUENCE: 14
cctngaaaat tgagagaagt ccaccacg                                    28
```